United States Patent [19]

Balaban et al.

[11] Patent Number: 5,433,711

[45] Date of Patent: Jul. 18, 1995

[54] SYRINGE WITH CANNULA-PROTECTING SHEATH AND SEALING CENTER ROD

[75] Inventors: Stephen M. Balaban, Chesterfield; Jonathan P. Smith, Pacific, both of Mo.

[73] Assignee: Monsanto Company, St. Louis, Mo.

[21] Appl. No.: 283,324

[22] Filed: Aug. 1, 1994

[51] Int. Cl.⁶ .......................... A61M 5/32; A61M 5/24
[52] U.S. Cl. ....................................... 604/192; 604/200
[58] Field of Search ............... 604/192, 199, 200, 218, 604/220, 282

[56] References Cited

U.S. PATENT DOCUMENTS

| | | | |
|---|---|---|---|
| 1,279,530 | 9/1918 | Fitting | 604/192 |
| 1,711,352 | 4/1929 | Jeffreys . | |
| 2,219,301 | 10/1940 | Erhard | 604/200 |
| 2,578,813 | 12/1951 | Kollsman . | |
| 2,668,534 | 2/1954 | Barradus et al. | 604/192 |
| 2,742,041 | 4/1956 | Lipari . | |
| 2,757,671 | 8/1956 | Haafkens | 604/200 |
| 3,559,645 | 2/1971 | Schaller . | |
| 5,199,952 | 4/1993 | Marshall et al. | 604/156 |

FOREIGN PATENT DOCUMENTS

| | | |
|---|---|---|
| 0510575A1 | 10/1902 | European Pat. Off. . |
| 776.968 | 2/1935 | France . |
| 1.003.347 | 3/1952 | France . |
| 63.246 | 9/1955 | France . |
| 2.082.127 | 10/1971 | France . |
| 639855 | 12/1936 | Germany . |
| 869411 | 6/1953 | Germany . |
| 412204 | 11/1966 | Switzerland . |
| 109040 | 11/1917 | United Kingdom . |
| 109041 | 11/1917 | United Kingdom . |
| 129650 | 11/1920 | United Kingdom . |
| 727348 | 3/1955 | United Kingdom . |
| 979124 | 1/1965 | United Kingdom . |
| 1150196 | 4/1969 | United Kingdom . |
| 1575551 | 9/1980 | United Kingdom . |
| 2195537 | 4/1988 | United Kingdom . |
| WO91/10423 | 7/1991 | WIPO . |

Primary Examiner—John D. Yasko
Assistant Examiner—Adam J. Cermak
Attorney, Agent, or Firm—George R. Beck; Gary M. Bond

[57] ABSTRACT

A syringe assembly is comprised of a plunger, a syringe barrel having a cannula collar at one end of the barrel and an interior chamber within the barrel, a hollow cannula secured within the syringe barrel collar with the cannula extending axially from the collar to its distal end, a bore extending axially through the cannula and the syringe barrel collar, a segment of the bore decreasing (e.g., tapering) in diameter as it extends in a direction from the distal end of the cannula toward the barrel interior chamber, and a sheath removably attached to the syringe barrel and covering the cannula, the sheath being affixed to a center rod extending axially from the sheath into the bore at the cannula distal end and then seating in a sealing engagement with said segment of the interior bore.

21 Claims, 1 Drawing Sheet

SYRINGE WITH CANNULA-PROTECTING SHEATH AND SEALING CENTER ROD

FIELD OF THE INVENTION

The present invention pertains to a syringe of the type that is prefilled with a substance for both storing the substance within the syringe and later ejecting the substance from the syringe, e.g., to inject the substance into the body of an animal. The syringe is comprised of a plunger, a syringe barrel, a cannula projecting from one end of the barrel or a cannula collar affixed thereto, and a removable sheath attached to the syringe barrel and covering the cannula to shield it from contamination and/or unwanted contacts prior to desired ejection of the substance from the syringe. A center bore extends through the cannula to the interior chamber of the syringe barrel. At least a segment of the bore changes (e.g., tapers) to a smaller diameter in the direction extending from the cannula distal end to the interior chamber of the syringe barrel. The sheath has a center rod affixed thereto that extends axially from the sheath through the cannula and seats in a sealing engagement with at least said segment of the interior bore, sealing the substance within the syringe barrel interior chamber until such time as ejection is desired.

The syringe of this invention has various advantages in addition to the cannula-shielding feature mentioned above. These advantages include greater ease of use, compared to commonly used techniques such as (1) affixing a cannula to a pre-filled syringe barrel before injecting the substance through the cannula and (2) draw-up of the injectable substance through a pre-attached cannula into the syringe barrel from which it is expelled during a subsequent injection. Other important advantages of the aforementioned sealing engagement are that it (1) prevents leakage of the substance from the syringe barrel into the sheath during storage of the syringe and (2) prevents any solid particles which settle or precipitate out of the substance stored in the syringe from accumulating in the cannula and then clogging or restricting flow of the substance through the cannula at the time of desired injection.

DESCRIPTION OF THE RELATED ART

There are various kinds of known prefilled syringes, e.g., those having interior chambers that store a substance prior to its ejection from the syringe. Prefilled syringes are often used where a large number of injections are to be made in as short a time period as possible and with as little difficulty as possible. Syringes of this type have found uses in injecting prophylactic, therapeutic and stimulative substances.

One example of a beneficial use of prefilled syringes is in injecting herds of livestock. For example, in a dairy herd containing many animals, use of prefilled syringes where each is used to inject a measured dose of a substance into one animal of the herd enables the injections of the herd to take place with a considerable savings of time and effort.

To reduce the cost of the disposable, prefilled syringes, they typically have a simple construction and are comprised of a syringe barrel with an interior chamber, a plunger inserted into the chamber at one end of the barrel, a cannula extending from the opposite end of the barrel, and in some instances a cannula cap or sheath. Over time, when particular substances are stored in the conventional syringe described above, for example a substance containing solids or particulate matter suspended or dissolved in a liquid or gel, the solids may settle out or precipitate in the form of particles that can collect in the interior bore of the cannula and clog the bore, thus preventing or restricting delivery of the substance through the cannula when that is desired, e.g., when the syringe plunger is pushed through the syringe barrel interior chamber to eject the substance from the syringe.

Certain prior art syringes have been constructed with rods extending through the center of the syringe cannula, some with a cap on the rod that seats over the cannula tip to prevent the substance stored in the syringe from leaking prematurely from the cannula. However, these prior art rods have been generally constructed with a diameter smaller than the diameter of the cannula bore. No steps have been taken to seal the cannula interior bore from the barrel interior chamber, even with the rod inserted through the bore. With such prior art devices, there is an undesirable potential for solid particles to settle or precipitate out of the substance stored in the syringe interior chamber and leak into and become lodged within the cannula, i.e., within the space between the interior bore of the cannula and the surface of the rod inserted in the interior bore. Although removal of the rod from the cannula will provide a flow path through the interior bore for the substance contained in the syringe interior chamber, solid particles that have settled or precipitated out of the substance and have become lodged along the interior surface of the cannula bore will slow and/or partially restrict the flow of the substance through the cannula bore as the syringe plunger is pushed to eject the substance from the syringe interior chamber.

SUMMARY OF THE INVENTION

The syringe of this invention is constructed with a syringe barrel having a hollow interior chamber. Generally, a cannula collar is provided at one end of the barrel and a plunger extends into the interior chamber at the opposite end of the barrel. The cannula is secured to the syringe barrel collar, and in a preferred embodiment is seated on a shoulder (e.g., circular) of the collar which prevents the cannula from being pushed into the syringe barrel, e.g., when a force is exerted on the distal end of the cannula when an injection is initiated. A hollow interior bore extends axially through the center of the cannula and through the syringe barrel collar as it extends from the cannula tip to the syringe barrel interior chamber.

Generally, a first segment of the interior bore has a substantially constant interior diameter as it extends through the length of the cannula. Normally, a second segment of the interior bore tapers to a smaller diameter, e.g., as it extends through the syringe barrel collar, although the decrease in diameter can be abrupt, if desired, rather than gradual. In a preferred embodiment, the second segment tapers from a first interior diameter that is substantially equal to the interior diameter of the bore within the cannula, to a second, smaller interior diameter of the bore segment at the exit of the bore into the syringe barrel interior chamber.

A sheath is attached removably (e.g., by force fit of a sheath made of a resilient material) to the syringe barrel and essentially completely covers the cannula. The sheath has a center rod affixed to the sheath in the sheath interior. The center rod is removably inserted into the bore at the cannula distal end and preferably, but not necessarily, extends through the complete length of the bore while the sheath is attached to the syringe barrel.

In a preferred embodiment, the center rod has a substantially constant exterior diameter along its length. The rod diameter is smaller than the interior diameter of the first segment of the bore, and is larger than the interior diameter of the second segment of the bore. Thus, as the center rod is inserted into and through the interior bore, the rod wedges within the bore at the location where the interior diameter of the bore becomes (e.g., tapers to) less than that of the rod, thus producing a seal.

Preferably, both the syringe barrel collar and the sheath center rod are constructed of resilient plastic material(s) that compress(es) slightly as the rod is wedged into the smaller-diameter segment of the bore, thereby providing a sealed engagement of the rod with that segment of the bore. This sealed engagement between the rod and the second segment of the bore is most desirably situated at the opening of the bore to the syringe barrel interior chamber, preventing any of the substance contained in the chamber from entering the bore until the rod is removed from the cannula.

BRIEF DESCRIPTION OF THE DRAWINGS

Further objects and features of the present invention are revealed in the following detailed description of the preferred embodiment of the invention and in the drawing figures wherein.

DESCRIPTION OF THE PREFERRED EMBODIMENTS

Figure 1:
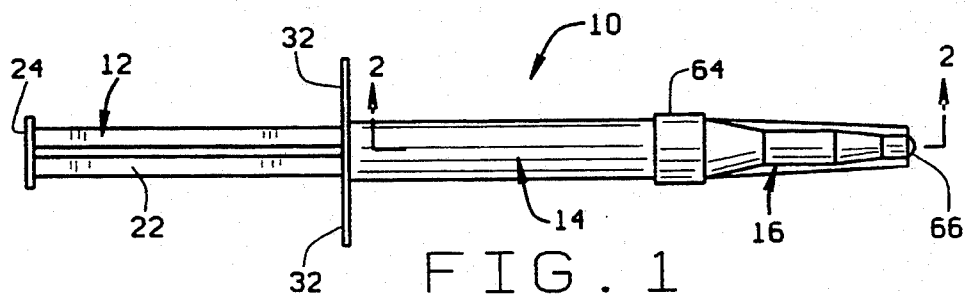
FIG. 1 is a side elevation view of the sheath and syringe of the present invention.

The syringe 10 of the present invention is shown assembled in FIG. 1. Basically, the syringe 10 is comprised of a syringe plunger 12, a syringe barrel 14 and a protective sheath 16. In the preferred embodiment of the invention, these basic component parts are all constructed of a resilient, plastic material, for example polyethylene or polypropylene. Plunger 12 is slidably received within the barrel 14, and sheath 16 is removably attached to the end of barrel 14. Plunger 12 includes an elongated rod 22 with a finger push tab 24 at one end and a sealing piston 26 at its opposite end (shown in FIG. 2).

The syringe barrel 14 has a cylindrical, tubular configuration with finger flanges 32 at one end and a cannula collar 34 at the axially opposite end of the elongated barrel 14. The interior chamber 36 of the barrel has a cylindrical interior surface dimensioned to receive the plunger piston 26 in sliding, sealing engagement therein.

The cannula 38 is supported in the cannula collar 34 of the syringe. The cannula 38 has an axial length with opposite proximal 42 and distal 44 ends. The proximal end 42 is secured within the collar 34 of the syringe barrel 14 by an adhesive 46 or in some other suitable manner. The cannula distal end 44 outside the collar 34 tapers to a sharpened end, e.g., a point. Typically, the cannula is constructed of a metal (e.g., stainless steel) and is from about 10 to about 18 (preferably about 16) gauge. The cannula has a cylindrical interior surface 48 that surrounds an interior bore 52 of the syringe, the interior bore 52 extending from the cannula distal end 44 through the cannula 38 and the collar 34 to the syringe barrel interior chamber 36.

The segment of the interior bore 52 that extends through the cannula between its distal 44 and proximal 42 ends has a constant interior diameter. The segment of the interior bore 52 that extends from the cannula proximal end 42 through the syringe collar 34 to the barrel interior chamber 36 tapers as it extends toward the interior chamber. This segment of the interior bore 52 is surrounded by an interior surface 54 of the syringe barrel collar 34 having a frustoconical configuration. As in FIGS. 3 and 4, the segment of the interior bore 52 surrounded by the collar interior surface 54 begins with an interior diameter substantially equal to that of the cannula interior surface 48 and tapers to an interior diameter less than that of the cannula interior surface as it extends toward the interior chamber 36 of the syringe barrel from the cannula proximal end 42.

Figure 2:
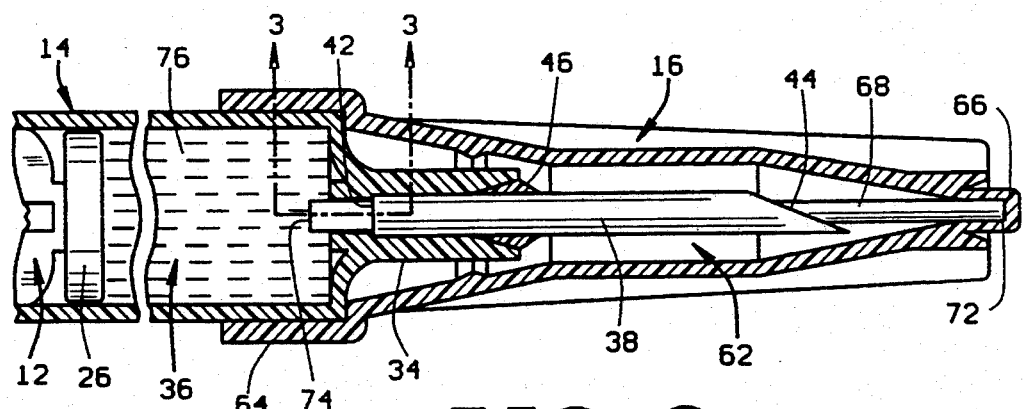
FIG. 2 is a partial view, in section, taken in a plane along the line 2—2 in FIG. 1, showing detail of the sheath and syringe of the invention.

The sheath 16 has an axial length with a hollow interior 62. A collar 64 surrounds an opening to the interior at one end of the sheath and the opposite end 66 of the sheath is closed. The collar 64 is configured to be releasably attached around the exterior of the syringe barrel 14 adjacent the collar 34, as in FIG. 2. The sheath interior 62 is sufficiently large to receive the syringe barrel collar 34 and the cannula 38 therein with the collar 64 removably attached over the exterior of the syringe barrel 14 as shown in FIG. 2.

A center rod 68 is affixed to the sheath 16 within its interior 62. The center rod 68 has an elongated configuration with a distal end 72 secured to the closed end 66 of the sheath and a proximal end 74 positioned outside the sheath interior 62. As seen in FIG. 2, the length of the rod is sufficient to project the rod proximal end 74 completely through the tapered segment of the interior bore 52 within the syringe barrel collar 34 with the sheath 16 attached to the exterior of the syringe barrel.

In a preferred embodiment of the invention, the center rod 68 has a cylindrical configuration with a constant diameter along its entire length. The diameter of the center rod 68 is less than the interior diameter of the segment of the interior bore 52 surrounded by the cannula interior surface 48, but is larger than the interior diameter of at least a portion of the segment of the interior bore 52 surrounded by the interior surface 54 of the syringe barrel collar 34. With these relative diameter dimensions of the sheath center rod 68 and the tapered segment of the interior bore 52 extending through the syringe barrel collar 34, at least portions of both the segment of the interior bore 52 extending through the syringe collar 34 and the sheath center rod 68 adjacent its proximal end 74 will compress when the rod 68 is inserted through the interior bore 52 and the sheath collar 64 is attached to the exterior of the syringe barrel 14 in the position shown in FIG. 2. This compression of both the collar interior surface 54 and the sheath center rod 68 produces a sealing engagement between the collar surface and center rod.

Figures 3, 4:
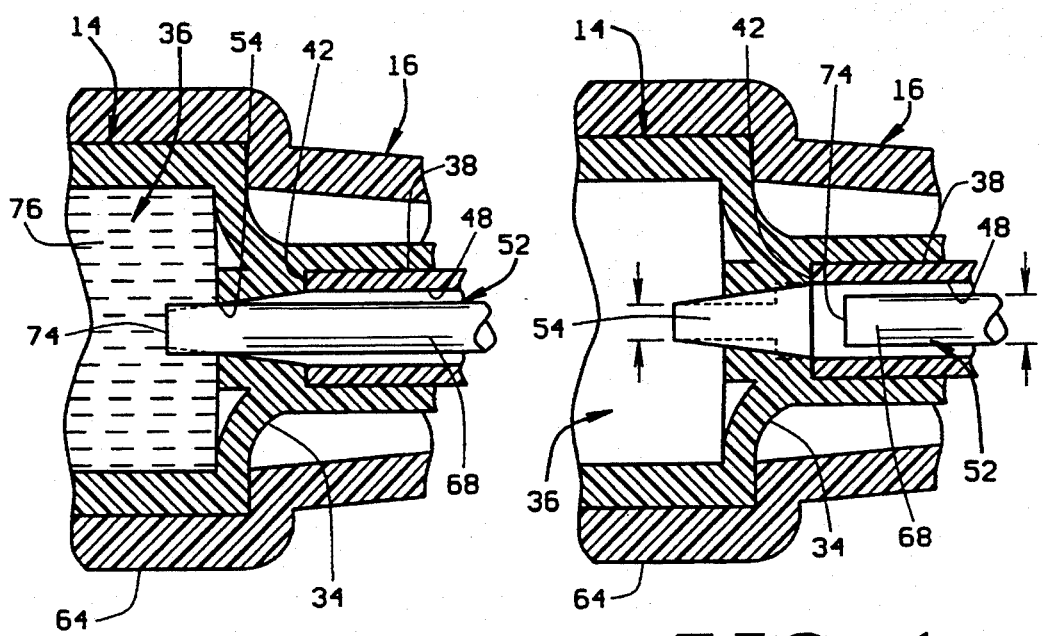
FIG. 3 is a partial view, in section, taken in a plane along the line 3—3 of FIG. 2; and, FIG. 4 is a partial view, in section, similar to that of FIG. 3 showing the sheath center rod withdrawn from the tapered portion of the syringe bore.

In a variant embodiment of the center rod 68, a portion of the rod adjacent its proxmial end 74 may be tapered slightly as shown in phantom lines in FIG. 3.

The taper is provided to assist in insertion of the rod proximal end 74 through the interior bore 52 at the cannula distal end 44 when attaching the sheath to the syringe barrel exterior. Such a taper of the end of rod 68 is especially advantageous if the diameter of the first segment of the bore decreases abruptly, rather than tapering, to the smaller diameter of the second bore segment.

In a further variant embodiment of the invention, the entire center rod 68 may be constructed of a material that is not resilient, for example a metal. As the sheath is assembled to the syringe barrel and the proximal end 74 of the rod is inserted through a tapered segment of the interior bore 52, e.g., within collar 34, the resilient compression of the material of the collar interior surface 54 around the center rod proximal end 74 provides a sealing engagement between the collar interior surface and the center rod.

In a further variant embodiment of the invention, the tapered segment of the collar interior surface is replaced by a necked down portion of the interior bore where the bore diameter changes abruptly from the first diameter to the second diameter at an annular wall that is perpendicular to the bore center axis. This embodiment is illustrated in dashed lines in FIG. 4. In this embodiment the tapered rod end 74 engages against the inner peripheral edge of the annular wall, thus producing a seal within the bore.

In all of the embodiments of the invention described above, with the sheath 16 removably attached to the syringe barrel 14 and the center rod 68 extending through the interior bore 52, the bore is sealed from the barrel interior chamber 36 preventing any substance 76 contained within the chamber from potentially blocking the interior bore 52.

What is claimed is:

1. In a syringe of the type that is prefilled with a substance for both storing the substance within the syringe and later ejecting the substance from the syringe, the improvement comprising:
   a syringe barrel having an axial length with a cannula collar at one end of the barrel length and an interior chamber within the barrel;
   a hollow cannula having axially opposite proximal and distal ends, the proximal end being secured to the syringe barrel collar with the cannula extending axially from the collar to its distal end;
   a bore having a length extending axially through the cannula and the syringe barrel collar between the cannula distal end and the syringe barrel interior chamber, the bore having an interior surface where at least a segment of the length of the bore changes in diameter from a first interior diameter of the bore to a second interior diameter of the bore, less than the first interior diameter, as the bore extends in the direction from the cannula distal end to the barrel interior chamber through the bore segment; and,
   a center rod having a diameter smaller than the first interior diameter and larger than the second interior diameter, removably inserted axially into the bore at the cannula distal end and seating in a sealing engagement with said segment of the interior bore.

2. The syringe of claim 1, further comprising:
   the bore interior surface along the segment of the bore tapers from the first interior diameter to the second interior diameter.

3. The syringe of claim 2, further comprising:
   a sheath removably attached to the syringe barrel and covering the cannula, the sheath being affixed to the center rod.

4. The syringe of claim 3, wherein:
   the rod has a length such that the rod length extends completely through the tapered segment of the bore.

5. The syringe of claim 3, wherein:
   the rod is constructed of a resilient material that is compressed within at least a portion of the tapered segment of the bore when the rod is inserted into the bore, thereby seating a portion of the rod in sealing engagement with said portion of the tapered segment of the bore.

6. The syringe of claim 5, wherein:
   the portion of the rod that seats in sealing engagement has a circular cross section having a diameter which, while the rod is not compressed, is larger than the second interior diameter of the interior bore.

7. The syringe of claim 6, wherein:
   the rod has an essentially constant cross section diameter along its length.

8. The syringe of claim 5, wherein:
   the tapered segment of the bore is within the collar and the collar is constructed of a resilient material that is compressed within at least a portion of the tapered segment of the bore while the sheath is attached to the syringe barrel, thereby seating a portion of the rod in sealing engagement with said portion of the tapered segment of the bore.

9. The syringe of claim 3, wherein:
   the tapered segment of the bore is within the collar and the collar is constructed of a resilient material that is compressed within at least a portion of the tapered segment of the bore while the sheath is attached to the syringe barrel, thereby seating a portion of the rod in sealing engagement with said portion of the tapered segment of the bore.

10. The syringe of claim 3, wherein:
    the rod has a length with a distal end inserted into the bore and a proximal end outside the bore and affixed to the sheath, and a portion of the rod length near its distal end has a cross section diameter smaller than that of a remainder of the rod length.

11. The syringe of claim 2, wherein:
    the tapered portion of the interior bore is adjacent the cannula proximal end and is spaced from the cannula distal end.

12. The syringe of claim 2, wherein:
    the bore between the cannula distal end and the tapered segment of the bore has an interior diameter equal to the first interior diameter.

13. The syringe of claim 2, wherein:
    the tapered segment of the bore is within the collar.

14. The syringe of claim 13, wherein:
    the collar is constructed of a resilient material that is compressed within at least a portion of the tapered segment of the bore while the rod is inserted into the bore thereby seating a portion of the rod in sealing engagement with the portion of the tapered segment of the bore.

15. The syringe of claim 2, wherein:
    the bore extends through the cannula between its distal and proximal ends and then through the barrel collar between the cannula proximal end and the barrel interior chamber.

16. The syringe of claim 2, wherein:

the rod length extends completely through the tapered segment of the bore.

17. The syringe of claim 2, wherein:

the rod is constructed of a resilient material that is compressed within said segment of the bore when the rod is inserted into the bore, thereby seating a portion of the rod in sealing engagement with said segment of the bore.

18. The syringe of claim 17, wherein:

the portion of the rod that seats in sealing engagement has a circular cross section with a cross section diameter which, while the rod is not compressed, is larger than the second interior diameter of the interior bore.

19. The syringe of claim 18, wherein:

the rod has a constant cross section diameter along its length.

20. The syringe of claim 17, wherein:

the tapered segment of the bore is within the collar and the collar is constructed of a resilient material that is compressed within at least a portion of the tapered segment of the bore when the rod is inserted into the bore, thereby seating a portion of the rod in sealing engagement with said portion of the tapered segment of the bore.

21. The syringe of claim 2, wherein:

the rod has a length with a distal end inserted into the bore and a proximal end outside the bore, and a portion of the rod length near its distal end has a cross section diameter smaller than that of a remainder of the rod length.

* * * * *